(12) United States Patent  (10) Patent No.: US 9,579,793 B2
Jacob et al.  (45) Date of Patent: Feb. 28, 2017

(54) ROBOT AND METHOD FOR CONTROLLING A ROBOT

(75) Inventors: Dirk Jacob, Marktoberdorf (DE); Tobias Ortmaier, Hemmingen (DE)

(73) Assignee: KUKA Roboter GmbH, Augsburg (DE)

(*) Notice: Subject to any disclaimer, the term of this patent is extended or adjusted under 35 U.S.C. 154(b) by 1486 days.

(21) Appl. No.: 13/060,847

(22) PCT Filed: Aug. 19, 2009

(86) PCT No.: PCT/EP2009/006009
§ 371 (c)(1),
(2), (4) Date: Apr. 11, 2011

(87) PCT Pub. No.: WO2010/025828
PCT Pub. Date: Mar. 11, 2010

(65) Prior Publication Data
US 2011/0184558 A1    Jul. 28, 2011

(30) Foreign Application Priority Data

Aug. 27, 2008   (DE) .................. 10 2008 041 602

(51) Int. Cl.
*B25J 9/16* (2006.01)
*A61B 34/30* (2016.01)
*A61B 17/00* (2006.01)

(52) U.S. Cl.
CPC ............. *B25J 9/1643* (2013.01); *A61B 34/30* (2016.02); *B25J 9/1676* (2013.01); *B25J 9/1689* (2013.01);
(Continued)

(58) Field of Classification Search
CPC ...... B25J 9/1689; B25J 9/1676; B25J 9/1643; A61B 34/30; A61B 2090/0427;
(Continued)

(56) References Cited

U.S. PATENT DOCUMENTS 4,490,660 A * 12/1984 Tsuchihashi .................. 700/255
5,150,026 A *  9/1992 Seraji et al. ............. 318/568.11
(Continued)

FOREIGN PATENT DOCUMENTS

DE   42 02 505 A1   8/1993
DE  198 10 341 A1   9/1999
(Continued)

OTHER PUBLICATIONS

Nic Fleming, "Dancing robot copies human moves", The Telegraph, Aug. 8, 2007.*
(Continued)

*Primary Examiner* — Abby Lin
(74) *Attorney, Agent, or Firm* — Wood Herron & Evans LLP

(57) ABSTRACT

The invention relates to a robot and a method for controlling a robot. The distance between an object and the robot and/or the derivative thereof or a first motion of the object is detected by means of a non-contact distance sensor arranged in or on a robot arm of the robot and/or on or in an end effector fastened on the robot arm. The robot arm is moved based on the first motion detected by means of the distance sensor, a target force or a target torque to be applied by the robot is determined based on the distance detected between the object and the robot, and/or a function of the robot or a parameterization of a function of the robot is triggered based on the first motion detected and/or a target distance between the object and the robot and/or the derivative thereof detected by means of the distance sensor.

11 Claims, 5 Drawing Sheets

(52) U.S. Cl.
CPC .............. *A61B 2017/00207* (2013.01); *A61B 2090/0427* (2016.02); *A61B 2090/061* (2016.02); *G05B 2219/39211* (2013.01); *G05B 2219/40116* (2013.01); *G05B 2219/40202* (2013.01); *G05B 2219/40617* (2013.01)

(58) Field of Classification Search
CPC .... A61B 2090/061; A61B 2017/00207; B05B 2219/39211; B05B 2219/40116; B05B 2219/40202; B05B 2219/20617
USPC .......................... 318/568.1–568.25; 382/153; 700/245–264; 901/2, 3, 46, 47, 50
See application file for complete search history.

(56) References Cited

U.S. PATENT DOCUMENTS

| | | | |
|---|---|---|---|
| 5,345,087 A * | 9/1994 | Luber et al. | 250/559.29 |
| 5,606,494 A | 2/1997 | Oshima et al. | |
| 6,175,610 B1 | 1/2001 | Peter | |
| 6,285,920 B1 | 9/2001 | McGee et al. | |
| 2002/0188379 A1* | 12/2002 | McGee et al. | 700/245 |
| 2007/0255454 A1 | 11/2007 | Dariush | |
| 2008/0021597 A1* | 1/2008 | Merte et al. | 700/255 |
| 2009/0171505 A1 | 7/2009 | Okazaki | |

FOREIGN PATENT DOCUMENTS

| | | |
|---|---|---|
| DE | 101 37 955 A1 | 2/2003 |
| DE | 101 62 412 A1 | 7/2003 |
| DE | 102 01 488 A1 | 7/2003 |
| DE | 102 16 023 A1 | 11/2003 |
| DE | 103 20 343 A1 | 12/2004 |
| DE | 10 2006 044 071 A1 | 4/2008 |
| JP | 58-112104 A | 7/1983 |
| JP | 5-345293 A | 12/1993 |
| JP | 11-226889 A | 8/1999 |
| WO | 03/044287 A2 | 5/2003 |
| WO | 2008/004487 A1 | 1/2008 |

OTHER PUBLICATIONS

Komainda and Hiller, "Control of Heavy Load Manipulators in Varying Environments", Automation and Robotics in Construction XVI, 1999.*

Nanayakkara et al, "Skillful Adaptation of a 7 DOF Manipulator to Avoid Moving Obstacles in a Teleoperated Force Control Task", 2001 IEEE.*

European Patent Office; Search Report in International Patent Application No. PCT/EP2009/006009 mailed Nov. 12, 2009; 6 pages.

* cited by examiner

ROBOT AND METHOD FOR CONTROLLING A ROBOT

TECHNICAL FIELD

The invention relates to a robot, and to a method for controlling a robot.

BACKGROUND

Robots are manipulating machines, which are equipped with useful tools for automatic handling of objects, and are programmable in a plurality of motion axes, in particular with regard to orientation, position and process sequence. Robots have essentially a robotic arm with a plurality of axes and levers, which are moved by drives. The drives are for example electric drives.

The robot or its robot arm can also be moved manually, for example by means of a hand-held device or by guiding it manually. In particular when moving the robot by guiding it manually, in the course of which a person for example pushes or pulls on the robot arm, the danger exists that by touching the robot arm the person guiding the robot will be contaminated by the robot. This is particularly disadvantageous when the robot is used in the medical environment.

SUMMARY

The object of the present invention is to create prerequisites for contact-free control of a robot.

The object of the invention is fulfilled by a method for controlling a robot, having the following procedural steps:
  detecting a first movement of an object by means of a non-contact distance sensor situated in or on a robot arm of a robot and/or on or in an end effector attached to the robot arm, or detecting the distance between the object and the robot or the latter's derivative by means of the distance sensor, and
  moving the robot arm on the basis of the first movement detected by means of the distance sensor, ascertaining a target force or target torque to be produced by the robot and/or its derivatives on the basis of the detected distance between the object and the robot and/or its derivative, or triggering a function of the robot and/or a parameterizing of a function of the robot on the basis of the detected first movement and/or on the basis of a target distance between the object and the robot detected by means of the distance sensor.

The target distance may be in particular a minimum distance.

The object of the invention is also fulfilled by a robot having
  a robot arm with a plurality of axes, an attaching device for attaching an end effector, and drives to move the axes,
  at least one non-contact distance sensor situated on or in the robot arm, and
  a control device coupled with the drives and the distance sensor, which is set up
    to move the robot arm by means of the drives on the basis of a first movement of an object detected by means of the distance sensor,
    to ascertain a target force or target torque to be produced by the robot on the basis of a distance between the object and the robot and/or the latter's derivative detected by means of the distance sensor, and/or
    to trigger a function of the robot and/or to parameterize a function of the robot on the basis of the first movement detected by means of the distance sensor and/or to trigger a function of the robot and/or to parameterize a function of the robot on the basis of a detected target distance and/or its derivative.

Alternatively, the distance sensor may also be situated in or on the end effector and coupled with the control device of the robot according to the invention.

Accordingly, it is possible to carry out the method according to the invention using the robots according to the invention.

According to the invention, the at least one non-contact distance sensor is accordingly situated in or on the robot arm, for example on its structure, or in or on the end effector. Non-contact distance sensors as such are generally known, and generate a signal assigned to the distance between an object and the non-contact distance sensor, in particular an electrical signal. It is then also possible from this signal to ascertain the first movement of the object and/or the velocity of the object relative to the robot, on the basis of a derivative of the signal assigned to the distance. The object may be in particular a person, for example operating the robot according to the invention, so that this person is enabled to control the robot without contact.

Non-contact distance sensors are for example capacitive distance sensors, or are based on other physical laws.

On the basis of the distance between the object and the robot ascertained or its derivative by means of the non-contact distance sensor, or the first movement of the object ascertained by means of the distance sensor, it is provided for example according to the invention to initiate for example the function of the robot and/or the parameterizing of the function of the robot. The derivative of the distance between the object and the robot is the speed between the object and the robot. A function of the robot may be for example activating and/or deactivating an end effector situated on the attaching device. That enables a person operating the robot according to the invention to control the function of the end effector, which is for example a tool guided or moved with the robot according to the invention, generally without contact, in particular to switch it on and off without contact, without using a control panel for example. This not only results in the person not needing to touch the robot according to the invention to activate the end effector, but can also result in easier operation of the robot according to the invention.

On the basis of the distance between the object and the robot or its derivative ascertained by means of the non-contact sensor, according to an alternative embodiment of the robot according to the invention or of the method according to the invention the control device in particular ascertains the target force or target torque to be produced. Because of the use of the non-contact distance sensor, a person operating the robot according to the invention can be enabled to set the target force or target torque to be produced by the robot according to the invention in a relatively simple way, not only without contact but also relatively simply, by intuition.

According to one variant of the method according to the invention, or according to one variant of the robot according to the invention, the target force or target torque to be produced is a target force or a target torque to be produced by an end effector situated on the robot arm. The control device of the robot according to the invention can then be set up to activate the axes via the drives so that the end effector situated on the attaching device produces the target force or the target torque.

According to one variant of the method according to the invention, the robot arm is moved in such a way that an attaching device of the robot arm or the tool center point of an end effector situated on the robot arm executes a second movement corresponding to the first movement of the object, on the basis of the detected first movement. The control device of the robot according to the invention can be set up for that purpose so that it moves the axes by means of the drives in such a way that the attaching device or the tool center point of the end effector executes a second movement corresponding to the first movement of the object, on the basis of the detected first movement. On the basis of this embodiment, the person operating the robot according to the invention is enabled to guide the robot without contact, by executing the first movement, on the basis of which the robot arm moves automatically in such a way that it moves the attaching device or the tool center point in accordance with the movement of the person. On the basis of this embodiment of the robot according to the invention, it is possible for a person, as an object, to change the position or location of the robot according to the invention by approaching it purposively, without touching the robot. Thus prerequisites are created for guiding the robot according to the invention without touching it, whereby potential contamination of the person guiding the robot according to the invention by touching the robot can be avoided.

According to another embodiment of the method according to the invention, the robot arm is moved on the basis of the detected first movement, in order to prevent a collision of the object with the robot arm and at the same time to keep the position of an attaching device of the robot arm or of the tool center point of an end effector situated on the robot arm constant. The control device of the robot according to the invention can accordingly be set up to move the axes via the drives on the basis of the detected first movement, in order to prevent collision of the object with the robot arm, but to keep the position of the attaching device or of the tool center point of the end effector constant. This is possible for example when the robot according to the invention is what is known as a redundant robot, so that it can execute a movement in its zero space. Zero space designates the joint angle space of the redundant robot, in which it is possible to reconfigure the robot joints in such a way that the situation (position and orientation) of the end effector of the robot in space remains unchanged. This embodiment of the robot according to the invention can be used for example in robot-supported surgery, in order for example to enable a person as object, for example a doctor, to have access to the operation zone without removing the robot according to the invention or interrupting an intervention being carried out with the robot according to the invention.

BRIEF DESCRIPTION OF THE DRAWINGS

Examples of exemplary embodiments of the invention are depicted in the accompanying schematic drawing. The figures show the following.

DETAILED DESCRIPTION

Figure 1:
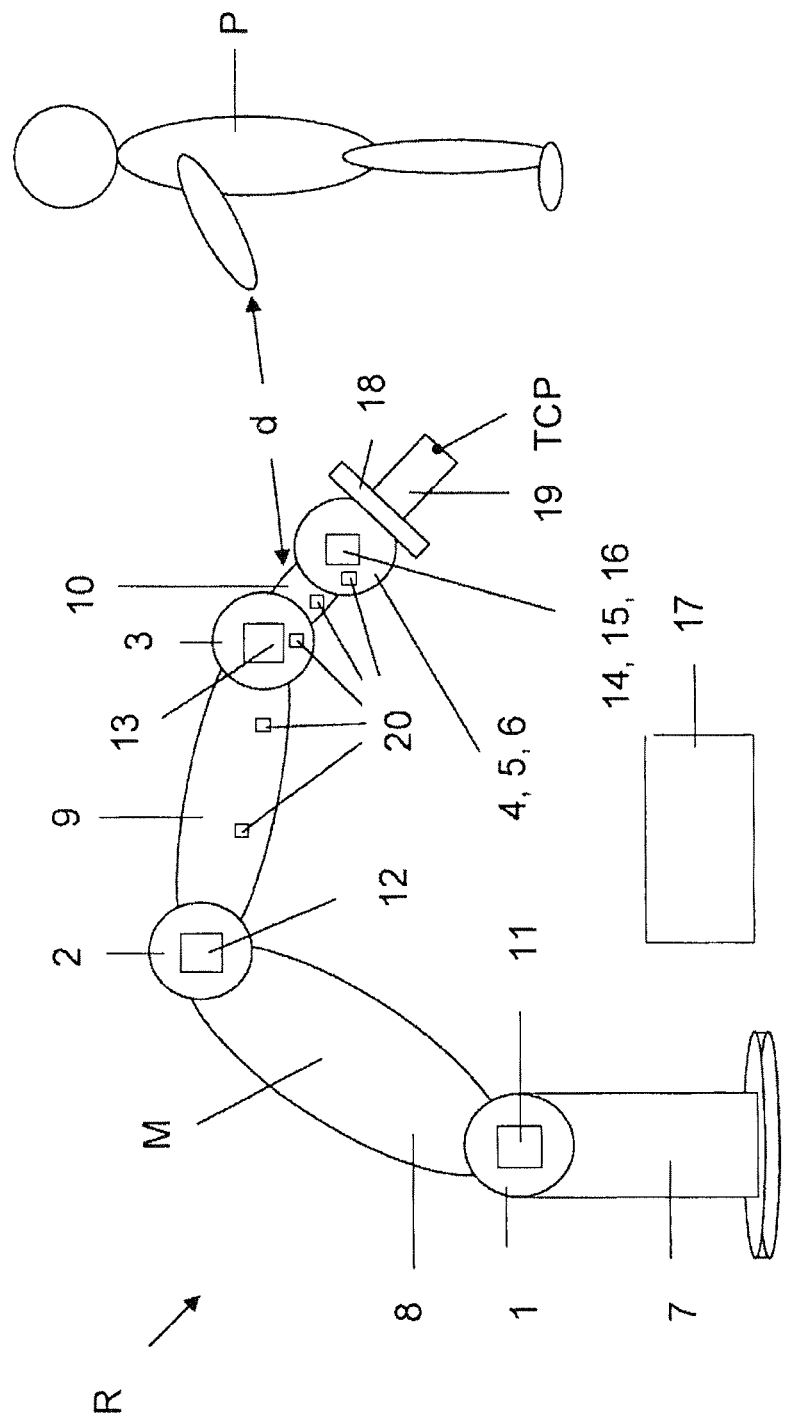
FIG. 1 a robot with non-contact distance sensors,
FIGS. 2, 3 an acquisition field of the non-contact distance sensors,
FIGS. 4-6 flow charts to illustrate the operation of the robot of FIG. 1,
FIG. 7 another robot,
FIG. 8 a flow chart to illustrate the operation of the robot of FIG. 7, and
FIG. 9 an end effector for a robot.

FIG. 1 shows a robot R with a robot arm M. Robot arm M represents essentially the movable part of robot R, and includes a plurality of axes 1-6, a plurality of levers 7-10 and a flange 18, to which an end effector 19, which is for example a medical instrument, in particular a surgical instrument, is attached.

Each of the axes 1-6 is moved with a drive, for example an electric drive 11-16, which are electrically connected in a non-depicted manner to a control computer 17 of robot R, so that control computer 17 or a computer program running on control computer 17 is able to activate electric drives 11-16 in such a way that the position or location of flange 18 of robot R or the tool center point TCP of robot R can be oriented essentially freely in space. Electric drives 11-16 of robot R each include for example an electric motor and possibly power electronics that activate the motors.

In the case of the present exemplary embodiment, robot R also has non-contact distance sensors 20 that are connected to control computer 17 in a non-depicted manner, which are situated in or on robot arm M, in particular integrated into the structure of robot arm M, or are set into an outer skin that encloses robot arm M, for example at individual spots or over a wide area. The non-contact distance sensors 20 are for example, as is the case in the present exemplary embodiment, capacitive distance sensors 20, which as such are known to a person skilled in the art. The distance sensors 20 are set up to ascertain a distance d to an object, for example to a person P.

Figure 2:
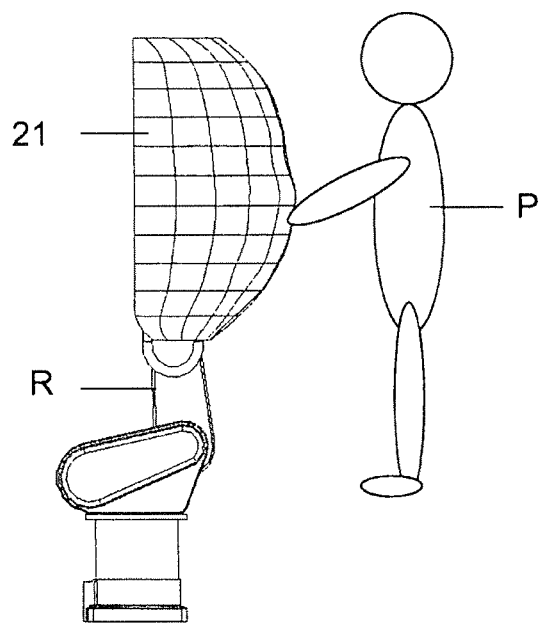
Figure 3:
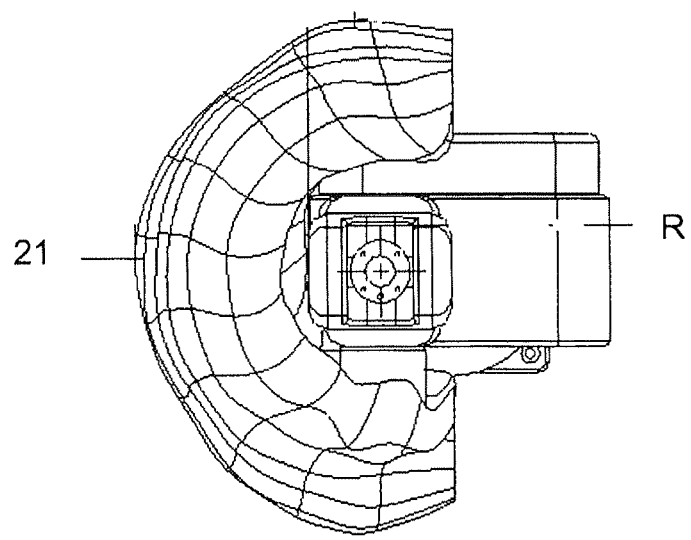

As just mentioned, in the case of the present exemplary embodiment the non-contact distance sensors 20 are capacitive distance sensors 20, which together produce an acquisition field 21 which at least partially encloses robot arm M and is depicted in FIGS. 2 and 3. FIG. 2 shows robot R with acquisition field 21 in a side view, and FIG. 3 shows robot R with acquisition field 21 in a top view.

If person P for example approaches this acquisition field 21, then distance sensors 20 generate a signal corresponding to the distance d between person P and robot R, which is transmitted to control computer 17 for further processing. In the case of the present exemplary embodiment, control computer 17 or a computer program running on control computer 17 controls the movement of robot R on the basis of this signal. This is summarized by means of a flow chart depicted in FIG. 4.

If person P approaches robot R, distance sensors 20 detect the distance d between robot R and person P. The signals assigned to distance d and coming from distance sensors 20 are transmitted to control computer 17, which recognizes a movement of person P on the basis of the signals, in particular on the basis of a detected change in the distance d between person P and robot R, step S1 of the flow chart in FIG. 4.

On the basis of the detected movement of person P, in the case of the present exemplary embodiment control computer 17 calculates a movement corresponding to the movement of person P, which is to be executed by effector 19 or its tool center point TCP, step S2 of the flow chart.

Figure 4:
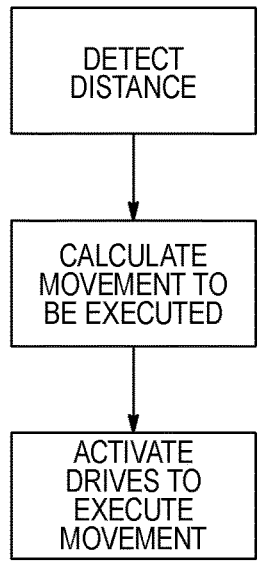

On the basis of the calculated movement that effector 19 or the tool center point TCP is to execute, control computer 17 activates drives 11-16 in such a way that effector 19 or tool center point TCP executes this movement without person P touching robot R, step S3 of the flow chart in FIG. 4.

In another exemplary embodiment, robot R or control compute 17 is configured so that a target force or target torque to be produced by robot R, and/or their respective derivatives, are calculated by means of the distance sensors 20. This is summarized by means of a flow chart depicted in FIG. 5.

If person P approaches robot R, distance sensors 20 detect the distance d between robot R and person P. The signals assigned to distance d and coming from distance sensors 20 are transmitted to control computer, step S1' of the flow chart in FIG. 5.

Figure 5:
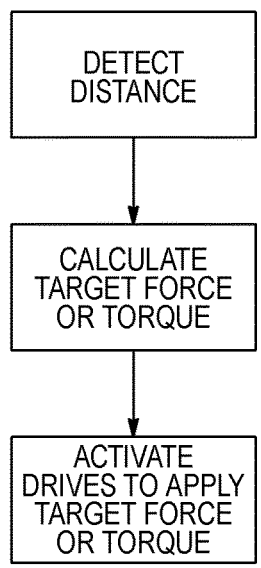

On the basis of the distance d, in the case of the present exemplary embodiment control computer 17 calculates a target force or target torque corresponding to the distance d, and/or their respective derivatives, which the end effector 19 situated on robot arm M is to produce, step S2' of the flow chart in FIG. 5.

Control computer 17 then activates drives 11-16 in such a way that end effector 19 applies the calculated target force to an object not depicted in further detail in the figures, step S3' of the flow chart in FIG. 5. Thus it is possible to set the force to be produced by end effector 19 and/or its derivative without contact, via the distance d to robot R. Alternatively, it is also possible to set a torque to be produced by end effector 19 and its derivative, instead of a force, via the distance d between person P and robot R.

In another exemplary embodiment, robot R or control computer 17 is configured so that a function of robot R and/or a parameterizing of a function of robot R is carried out automatically if the distance d between person P and robot R falls below a minimum distance or exceeds a maximum distance. This is summarized by means of a flow chart depicted in FIG. 6.

If person P approaches robot R so that distance d falls below the minimum distance, then this is detected by the distance sensors 20 or by control computer 17, step A1 of the flow chart in FIG. 6.

Figure 6:
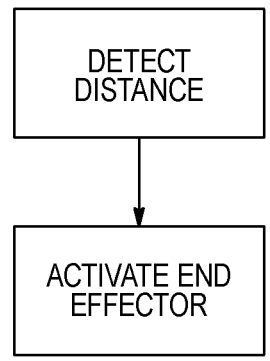

In the case of the present exemplary embodiment, control computer 17 then activates end effector 19, step A2 of the flow chart in FIG. 6.

Figure 7:
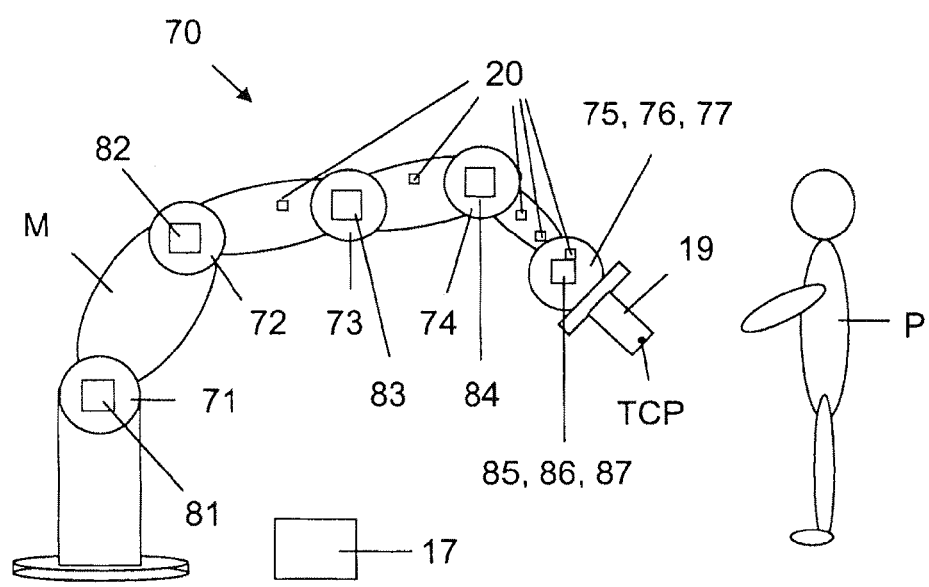

FIG. 7 shows another robot 70, with a robot arm M having a plurality of axes. Robot 70 in the case of the present exemplary embodiment is a redundant robot R, for which reason it is able to execute a movement in its zero space. Zero space designates the joint angle space of redundant robot 70, in which it is possible to reconfigure robot joints 71-77 in such a way that the situation (position and orientation) of end effector 19 in space remains unchanged. This embodiment of robot 70 can be used for example in robot-supported surgery.

In the case of the present exemplary embodiment, person P can operate robot 70 as follows, which is illustrated by means of a flow chart depicted in FIG. 8.

Figure 8:
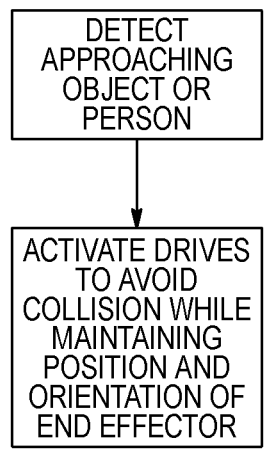

If person P approaches robot 70, this is detected by means of the distance sensors 20, step A1' of the flow chart in FIG. 8, for example by deriving the signal assigned to the distance.

To prevent a collision of person P with the relevant part of robot 70, control computer 17 activates drives 81-87 of robot 70 on the basis of the detected approach of person P to robot 70, in such a way that on the one hand the location of end effector 19 in space remains unchanged, the relevant lever or the relevant joint 71-77 with which person P potentially will collide yields to the approach of person P, step A2' of the flow chart in FIG. 8.

Figure 9:
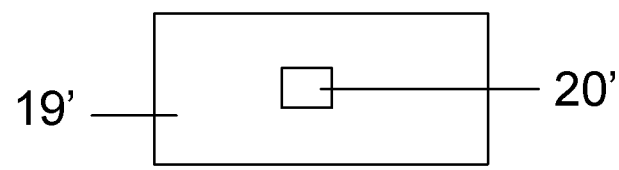

The robots R, 70 described above include the distance sensors 20, which are situated in or on the corresponding robot arms M. But it is also possible, additionally or alternatively, to situate the distance sensors 20 on the end effector. FIG. 9 shows such an end effector 19', in which or on which distance sensors 20' are situated.

What is claimed is:

1. A method of controlling a robot having at least one robot arm, the method comprising:
   detecting with a non-contact distance sensor a first movement of an object;
   wherein the non-contact distance sensor is attached to at least one of the robot arm or an end effector attached to the robot arm;
   moving the robot arm on the basis of the detected first movement in a manner that prevents collision between the robot arm and the object; and
   maintaining the position and orientation of an attaching device of the robot arm or of a tool center point of the end effector while moving the robot arm in the manner that prevents collision.

2. The method of claim 1, further comprising:
   in response to the detected movement, performing at least one of:
      triggering a robot function based at least on the detected movement, or
      parameterizing a robot function based at least on the detected movement.

3. The method of claim 1, further comprising:
   detecting a distance between the object and the robot with the non-contact distance sensor; and
   in response to the detected distance, performing at least one of:
      determining a target force or torque to be produced by the robot based on at least one of the detected distance or the derivative of the detected distance,
      triggering a robot function based on at least one of the detected distance or the derivative of the detected distance, or
      parameterizing a robot function based on at least one of the detected distance or the derivative of the detected distance.

4. The method of claim 3, wherein a target force or torque is determined and the method further comprises actuating the robot arm such that the end effector produces the determined target force or torque.

5. The method of claim 2, wherein the robot function is at least one of an activation or deactivation of the end effector.

6. The method of claim 3, wherein the robot function is at least one of an activation or deactivation of the end effector.

7. The method of claim 1, wherein the non-contact distance sensor is a capacitive distance sensor.

8. A robot, comprising:
   a robot arm including a plurality of articulation axes, an attaching device for attaching an end effector to the robot arm, and a plurality of drives for moving the robot arm about the respective axes;
   at least one non-contact distance sensor operatively coupled with the robot arm or an end effector attached to the robot arm; and
   a control device communicating with the drives and the sensor, the control device configured to actuate the drives to move the robot arm based on a first movement of an object detected by the at least one sensor;

the control device actuating the drives to move the robot arm in a manner that prevents collision between the robot arm and the object while maintaining a position and orientation of an attaching device of the robot arm or of a tool center point of the end effector.

9. The robot of claim 8, wherein the control device is further configured to perform at least one of:

determining a target force or torque to be produced by the robot based on at least one of a distance between the robot and the object detected by the at least one sensor, or on a derivative of the detected distance;

triggering a robot function based on at least one of the detected first movement, the detected distance, or the derivative of the detected distance; or parameterizing a robot function based on at least one of the detected first movement, the detected distance, or the derivative of the detected distance.

10. The robot of claim 9, wherein:

the robot function is at least one of an activation or deactivation of an end effector attached to the robot arm; and/or the control device actuates the robot arm such that the end effector produces the determined target force or torque.

11. The robot of claim 8, wherein the non-contact distance sensor is a capacitive distance sensor.

\* \* \* \* \*